US012108991B2

(12) United States Patent
Kaethner et al.

(10) Patent No.: US 12,108,991 B2
(45) Date of Patent: Oct. 8, 2024

(54) CONTROL OF A ROBOTICALLY MOVED OBJECT

(71) Applicant: Siemens Healthcare GmbH, Erlangen (DE)

(72) Inventors: Christian Kaethner, Forchheim (DE); Andreas Meyer, Bubenreuth (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/231,134

(22) Filed: Apr. 15, 2021

(65) Prior Publication Data

US 2021/0322105 A1 Oct. 21, 2021

(30) Foreign Application Priority Data

Apr. 21, 2020 (DE) .................. 10 2020 204 985

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/4218* (2013.01); *A61B 34/25* (2016.02); *A61B 90/37* (2016.02); *A61B 2034/2063* (2016.02)

(58) Field of Classification Search
CPC ...... A61B 2034/107; A61B 2034/2063; A61B 2090/3762; A61B 34/20; A61B 34/25; A61B 8/0841; A61B 8/4218; A61B 90/37
See application file for complete search history.

(56) References Cited

U.S. PATENT DOCUMENTS 7,974,681 B2   7/2011  Wallace et al.
9,237,930 B2   1/2016  Hauck
(Continued)

FOREIGN PATENT DOCUMENTS

CN     101524279 A    9/2009
CN     105246429 A    1/2016
(Continued)

OTHER PUBLICATIONS

German Office Action for German Application No. 10 2020 204 985.8 dated Mar. 17, 2021.

*Primary Examiner* — Michael T Rozanski
(74) *Attorney, Agent, or Firm* — Harness, Dickey & Pierce, P.L.C.

(57) ABSTRACT

A medical imaging system includes a medical imaging device to map a mapping region inside an examination object, the medical imaging device being designed such that a location of the mapping region is changable in respect of the examination object; and a processing device, including a data interface, to robotically position a medical object inside the examination object, via a movement device. In an embodiment, the processing device is configured to determine an instantaneous position of the medical object; specify a target position for the medical object, the target position being defined relative to the mapping region; determine one or more control signals, configured to cause a movement of the medical object via the movement device from the instantaneous position to the target position; and provide the one or more control signals, via the data interface, to the movement device.

28 Claims, 3 Drawing Sheets

(51) Int. Cl.
*A61B 34/00* (2016.01)
*A61B 90/00* (2016.01)

(56) References Cited

U.S. PATENT DOCUMENTS

| | | |
|---|---|---|
| 2004/0015053 A1 | 1/2004 | Bieger et al. |
| 2004/0019447 A1 | 1/2004 | Shachar |
| 2005/0256398 A1 | 11/2005 | Hastings et al. |
| 2006/0258935 A1 | 11/2006 | Pile-Spellman et al. |
| 2007/0025508 A1 | 2/2007 | Ohishi |
| 2007/0265518 A1 | 11/2007 | Boese et al. |
| 2008/0281181 A1 | 11/2008 | Manzione et al. |
| 2009/0082784 A1 | 3/2009 | Meissner et al. |
| 2009/0137952 A1 | 5/2009 | Ramamurthy et al. |
| 2009/0192385 A1 | 7/2009 | Meissner et al. |
| 2010/0069833 A1 | 3/2010 | Wenderow et al. |
| 2011/0230758 A1 | 9/2011 | Eichler |
| 2012/0215094 A1 | 8/2012 | Rahimian et al. |
| 2012/0238871 A1 | 9/2012 | Pfister |
| 2013/0231631 A1 | 9/2013 | Murphy et al. |
| 2014/0039305 A1 | 2/2014 | Wenderow et al. |
| 2014/0088404 A1 | 3/2014 | Gross |
| 2014/0309658 A1 | 10/2014 | Murphy et al. |
| 2015/0342556 A1 | 12/2015 | Van Dijk |
| 2016/0175057 A1 | 6/2016 | Ibach et al. |
| 2016/0354057 A1* | 12/2016 | Hansen ................. A61B 8/483 |
| 2017/0348060 A1 | 12/2017 | Blacker |
| 2018/0185099 A1 | 7/2018 | Kottenstette et al. |
| 2019/0231436 A1 | 8/2019 | Panse et al. |
| 2020/0170720 A1 | 6/2020 | Ummalaneni |
| 2020/0281667 A1 | 9/2020 | Blondel et al. |
| 2021/0315649 A1* | 10/2021 | Kaethner ................. A61B 6/12 |
| 2022/0061783 A1* | 3/2022 | Kaethner ................. G06T 15/08 |
| 2022/0270247 A1* | 8/2022 | Wiets ..................... A61B 90/37 |

FOREIGN PATENT DOCUMENTS

| | | |
|---|---|---|
| CN | 105744892 A | 7/2016 |
| CN | 106999250 A | 8/2017 |
| CN | 108474837 A | 8/2018 |
| CN | 110573105 A | 12/2019 |
| DE | 10025285 A1 | 12/2001 |
| DE | 102005028744 A1 | 2/2006 |
| DE | 102013109677 A1 | 3/2015 |
| EP | 2931127 A1 | 10/2015 |
| EP | 3406291 A1 | 11/2018 |
| WO | WO 2004006795 A1 | 1/2004 |
| WO | WO-2006124148 A2 | 11/2006 |
| WO | WO-2014/097086 A1 | 6/2014 |

* cited by examiner

CONTROL OF A ROBOTICALLY MOVED OBJECT

PRIORITY STATEMENT

The present application hereby claims priority under 35 U.S.C. § 119 to German patent application number DE 102020204985.8 filed Apr. 21, 2020, the entire contents of which are hereby incorporated herein by reference.

FIELD

Example embodiments of the invention generally relate to a method of controlling a robotically moved object.

BACKGROUND

Interventional medical procedures in or via a vessel system of an examination object often require, in particular percutaneous, introduction of a medical object into the vessel system. Furthermore, for a successful diagnosis and/or treatment it is often necessary to guide at least part of the of the medical object towards a target region in the vessel system that is to be treated.

For this, the medical object is often moved, in particular manually, by a medical operator (hereinafter also: user) with regular radiographic monitoring. One disadvantage of this is the high exposure of the medical operator and the examination object to X-ray radiation.

Ultrasound systems for imaging are used in different intervention systems for carrying out interventional medical procedures, therefore. An ultrasonic head is brought into contact with the surface of the skin of the patient in order to depict the underlying tissue and optionally the medical object. For this, the user has to guide the ultrasonic head manually in order to set the correct view of the vessel to be treated.

SUMMARY

This task has to be carried out by an ultrasound specialist while the surgeon performing the procedure introduces the guide wire or another medical object into the body, typically via the groin (femoral access) of the patient and then navigates it to the target area to be treated. The inventors have discovered that, in order to keep the medical object in the field of view of the imaging, this procedure demands a high level of personnel and operating stress due to the constant manual tracking of the imaging.

At least one embodiment of the invention is directed to enabling simplified and intuitive imaging-based operation of imaging systems and intervention systems in the case of an interventional medical procedure.

Embodiments of the invention are directed to an imaging system, an intervention system and a method for control of the imaging system or intervention system. Advantageous developments are disclosed in the claims.

According to one embodiment of the invention, a medical imaging system is provided. The imaging system has a medical imaging unit for mapping a mapping region inside an examination object, wherein the imaging unit is designed in such a way that the location of the mapping region can be changed in respect of the examination object. The imaging system also has a processing unit, which has a data interface to a movement device for robotic positioning of a medical object inside the examination object. The processing unit is also designed in such a way that it determines an instantaneous position of the medical object. The processing unit is also designed in such a way that it specifies a target position for the medical object defined relative to the mapping region. The processing unit is also designed to determine one or more control signal(s) which are capable of causing a movement of the medical object from the instantaneous position to the target position by way of the movement device. Furthermore, the processing unit is designed to provide the one or more control signal(s) via the data interface to the movement device.

According to a further embodiment, an intervention system for carrying out an interventional, in particular medical, procedure is provided. The intervention system has the above-described imaging system and the movement device for robotic positioning of the medical object inside the examination object and relative thereto.

According to a further embodiment, a method for control of an imaging or intervention system according to the aspects and embodiments is provided. The method has the following steps: acquiring image data of a mapping region inside the examination object via the imaging unit; determining an instantaneous position of the medical object; specifying a target position for the medical object, which target position is defined relative to the mapping region (in other words, is defined based upon the mapping region or based on the mapping region or is defined in specified relative location to the mapping region); determining one or more control signal(s) for the movement device, which one or more control signal(s) are capable of causing the movement device to move the medical object from the instantaneous position to the target position; providing the one or more control signal(s) to the movement device via the data interface.

In a further embodiment, the invention relates to a computer program product, which comprises a program and can be loaded directly into a memory of a programmable arithmetic unit and has program segments, for example libraries and help functions, in order to carry out a method for control of an intervention systems, in particular according to the embodiment, when the computer program product is executed. The computer program product can comprise software with a source code, which still has to be compiled and linked or which just has to be interpreted, or an executable software code, which just has to be loaded into the processing unit for execution. As a result of the computer program product, the method for control of a medical imaging device can be carried out quickly, in a manner that can be repeated identically and robustly.

The computer program product is configured such that it can perform an embodiment of the inventive method steps by way of the processing unit. The processing unit has in each case to exhibit the prerequisites such as, for example, an appropriate main memory, an appropriate graphics card or an appropriate logic unit, so the respective method steps can be performed efficiently.

In an embodiment, the computer program product is stored, for example, on a computer-readable medium or stored on a network or server from where it can be loaded into the processor of a processing unit, which can be directly connected to the processing unit or be designed as part of the processing unit. Furthermore, control information of the computer program product can be stored on an electronically readable data carrier. The control information of the electronically readable data carrier can be configured in such a way that it carries out an embodiment of the inventive method when the data carrier is used in a processing unit. Examples of electronically readable data carriers are a DVD, a magnetic tape or a USB stick on which electronically readable control information, in particular software, is stored. When this control information is read from the data carrier and stored in a processing unit, all inventive embodiments of the above-described methods can be carried out. At least one embodiment of the invention can thus also start from said computer-readable medium and/or said electronically readable data carrier. The advantages of the proposed computer program product substantially correspond to the advantages of the proposed method.

In a further embodiment, the invention relates to a medical imaging system, comprising:

a medical imaging device to map a mapping region inside an examination object, the medical imaging device being designed such that a location of the mapping region is changable in respect of the examination object; and a processing device, including a data interface, to robotically position a medical object inside the examination object, via a movement device, the processing device being configured to determine an instantaneous position of the medical object, specify a target position for the medical object, the target position being defined relative to the mapping region, determine one or more control signals, configured to cause a movement of the medical object via the movement device from the instantaneous position to the target position, and provide the one or more control signals, via the data interface, to the movement device.

In a further embodiment, the invention relates to an intervention system for carrying out an interventional medical, procedure, comprising:

the imaging system of an embodiment; and the movement device for robotic positioning of the medical object inside the examination object.

In a further embodiment, the invention relates to a method for control of an imaging system, comprising:

acquiring image data of a mapping region inside the examination object via an imaging device;

determining an instantaneous position of a medical object;

specifying a target position for the medical object, the target position being defined relative to the mapping region;

determining one or more control signals for a movement device, the one or more control signals being configured to cause a movement of the medical object from the instantaneous position to the target position via the movement device; and providing the one or more control signals to the movement device via a data interface.

In a further embodiment, the invention relates to a non-transitory computer program product, storing a program, directly loadable into a memory of a programmable arithmetic device of a processing device, the program including program segments to carry out a method of an embodiment when the program is executed in the arithmetic device of the processing device.

BRIEF DESCRIPTION OF THE DRAWINGS

Further specifics and advantages of the invention will become obvious from the following explanations of example embodiments with reference to schematic drawings. Modifications mentioned in this connection can be combined with each other respectively in order to form new embodiments. Identical reference numerals will be used for identical features in different figures.

In the drawings.

DETAILED DESCRIPTION OF THE EXAMPLE EMBODIMENTS

Figure 1:
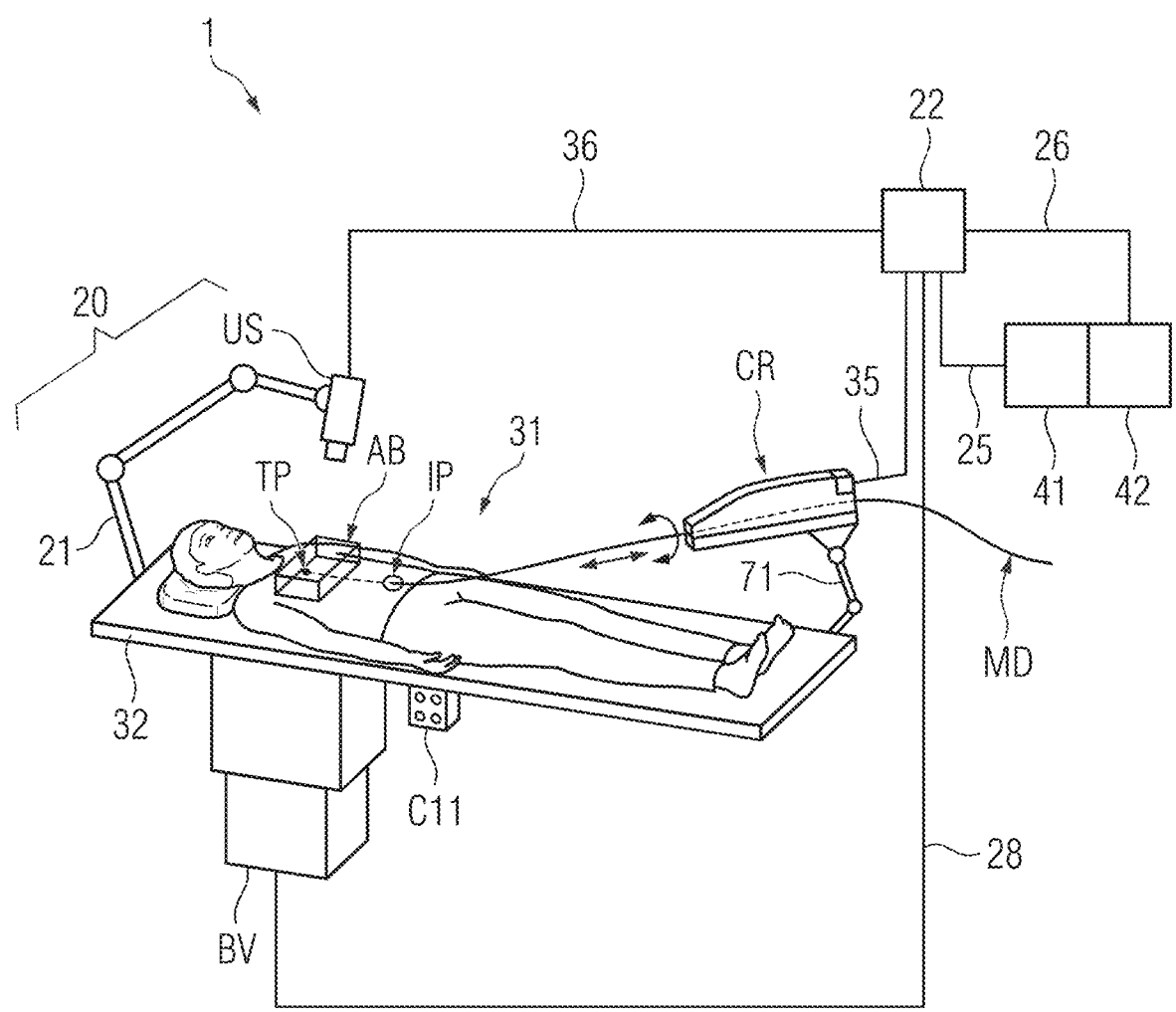
FIG. 1 shows a schematic presentation of an embodiment of the proposed system for imaging a robotically moved medical object.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to one embodiment of the invention, a medical imaging system is provided. The imaging system has a medical imaging unit for mapping a mapping region inside an examination object, wherein the imaging unit is designed in such a way that the location of the mapping region can be changed in respect of the examination object. The imaging system also has a processing unit, which has a data interface to a movement device for robotic positioning of a medical object inside the examination object. The processing unit is also designed in such a way that it determines an instantaneous position of the medical object. The processing unit is also designed in such a way that it specifies a target position for the medical object defined relative to the mapping region. The processing unit is also designed to determine one or more control signal(s) which are capable of causing a movement of the medical object from the instantaneous position to the target position by way of the movement device. Furthermore, the processing unit is designed to provide the one or more control signal(s) via the data interface to the movement device.

According to a further embodiment, an intervention system for carrying out an interventional, in particular medical, procedure is provided. The intervention system has the above-described imaging system and the movement device for robotic positioning of the medical object inside the examination object and relative thereto.

The medical object can be designed, for example, as a therapeutic or surgical instrument and/or diagnostic instrument. In particular, the medical object can be elongate and/or flexible. The medical object can be designed, for example, as a catheter and/or endoscope and/or guide wire. The medical object can have a predefined section, which is arranged preferably at a distal end of the medical object. The predefined section can be an actuator of the medical object or be arranged in the vicinity of the actuator. The actuator can be designed for performance of a therapeutic or surgical and/or diagnostic task inside the examination object. The actuator can be designed, for example, as a catheter tip and/or optical input of an endoscope and/or guide wire tip and/or tissue manipulator.

The examination object can be designed, for example, as an anatomical body with one or more cavities. In particular, the examination object can be a patient.

The medical imaging unit can be designed, for example, as a medical X-ray apparatus, in particular as a medical C-arm X-ray apparatus, and/or as a computed tomography system (CT) and/or as a sonography system and/or as a magnetic resonance tomography system (MRT) and/or as a positron emission tomography system (PET). Advantageously, the imaging unit can be moved relative to the examination object and/or relative to the movement device.

Furthermore, the imaging unit can be designed to map at least a section (or detail) of the examination object. This section or detail will also be called mapping region hereinafter. For this, the imaging unit can be designed to acquire, in particular, two-dimensional and/or three-dimensional and/or four-dimensional image data of the examination object. The three-dimensional image data can have, for example, two spatial dimensions and one temporal dimension (in the form of an image data sequence or a video) or three spatial dimensions. The four-dimensional image data can have, for example, three spatial dimensions and one temporal dimension (in the form of an image data sequence or a video). The two-dimensional image data can have, for example, two spatial dimensions.

The location of the mapping region can designate, in particular, the two- or three-dimensional region of the examination object from which image data is acquired. The location can consequently designate the arrangement of the mapping region in the examination object. The location can be defined in respect of the examination object, for example in the coordinates of the examination object or relative thereto, therefore.

The imaging unit can also be designed to map at least part of the medical object, in particular the predefined section and/or a marker structure provided on the medical object for improved visualization, in the image data.

Advantageously, the movement device can be a robotic device, which is designed for remote manipulation of the medical object, for example a catheter robot. Advantageously, the movement device can have a fastening element, in particular a movable and/or displaceable one. Furthermore, the movement device can have a cassette element, which is designed for receiving at least part of the medical object.

Furthermore, the movement device can have a movement element, which is fastened to the fastening element, for example a stand and/or robotic arm. In addition, the fastening element can be designed to fasten the movement element to a patient supporting device.

Furthermore, the movement element can advantageously have at least one actuator element, for example an electric motor, with the processing unit being designed for controlling the actuator element. Advantageously, the cassette element can be coupled, in particular mechanically and/or electromagnetically and/or pneumatically, to the movement element, in particular the at least one actuator element. The cassette element can also have at least one transmission element, which can be moved by way of the coupling between the cassette element and the movement element, in particular the at least one actuator element.

In particular, the at least one transmission element can be movement-coupled to the at least one actuator element. Advantageously, the transmission element is designed to transmit a movement of the actuator element to the medical object in such a way that the medical object is moved along a longitudinal extension direction of the medical object and/or that the medical object is rotated around the longitudinal extension direction. The at least one transmission element can have, for example, a pulley and/or roller and/or slit.

Advantageously, the movement element can have a plurality of, in particular independently controllable, actuator elements. Furthermore, the cassette element can have a plurality of transmission elements in particular at least one movement-coupled transmission element for each of the actuator elements. This can enable, in particular independent and/or simultaneous, movement of the medical object along different degrees of freedom of movement.

Advantageously, the movement device is arranged outside of the examination object. Furthermore, the movement device can be designed to control and/or move at least one section of the medical object, which is arranged in the examination object (which section can have one or more actuator(s)).

The processing unit can be designed as a central or decentral control of the imaging system or intervention system. The processing unit can have one or more control device(s) and/or one or more processor(s). The processing unit can be implemented as a local or Cloud-based processing server.

Advantageously, the processing unit can have at least one user interface. The user interface can have an input element, for example a keyboard and/or a joystick and/or a pedal and/or a capacitive and/or resistive and/or a combination of resistive and capacitive input field(s) and/or a pushbutton, which enables control of the intervention system by a user, for example a medical operator, by way of a corresponding operator input. This can enable control of the movement of the medical object in the examination object via the movement device and/or the imaging unit by way of a user input at the input element. The user interface can also have a presentation element, for example a monitor or a display. The presentation element can be designed to graphically present the mapping region (image data acquired from the mapping region) for a user.

The data interface can be designed as a real or virtual data interface. In particular, the data interface can be designed as a data interface for wireless data transfer. The data interface can have a hardware and/or software interface, for example a PCI bus, a USB interface, a Fire-Wire interface, a ZigBee or a Bluetooth interface. The data interface can have an interface of a communications network, wherein the communications network can have a Local Area Network (LAN), for example an Intranet or a Wide Area Network (WAN). Accordingly, the data interface can have a LAN interface or a Wireless LAN interface (WLAN or Wi-Fi). Furthermore, the data interface can also have a plurality of said interfaces in combination.

The instantaneous position can designate the position of the medical object relative to the locational state and/or the examination object and/or the mapping region. The instantaneous position can be given in the coordinates of the mapping region and/or relative thereto. The instantaneous position can be defined in the coordinates of the examination object or of the mapping region or relative thereto. The processing unit can be designed to determine the instantaneous position based on suitable movement information of the medical object. For this, the processing unit can be designed to receive the movement information (for example from the movement device). The processing unit can be designed to establish a registration between examination object or imaging unit and the movement device (for example via the data interface). The instantaneous position can relate, in particular, to the instantaneous position of the predefined section.

The target position can be taken to mean that position to which the medical object (or that of the predefined section) should be moved. The target position can be defined relative to the mapping region and preferably inside the mapping region. Once the target position is defined relative to the mapping region, for example a change in location of the mapping region relative to the examination object changes the target position in the examination object thereby. "Defined relative to the mapping region" can mean that the target position has a specified relative location to the mapping region. The specified relative location can be predetermined or firmly specified. Alternatively, the relative location, can be variably specified, for example based on a user input.

The components of the device cooperate synergistically to the extent, therefore that a position control of the medical object can be effected by a definition of a target position via the imaging. The target position can be tracked in particular with the mapping region, therefore. In other words, control of the medical object by way of a "method" of imaging or by direct specification of the target position using the output image data is possible thereby, and this enables intuitive and less resource-intensive implementation of an interventional procedure on an examination object within the meaning of the expressed object.

According to one embodiment, the processing unit is designed in such a way that the specification of the target position defined relative to the mapping region can be activated and/or deactivated. In other words, tracking of the target position with the mapping region (or with the location of the mapping region) can be switched on and off. Preferably, the processing unit is designed in such a way that the specification of the target position defined relative to the mapping region can be activated and/or deactivated by a user input. For this, the imaging system can have a user interface, which is designed in such a way that a user can activate and/or deactivate the specification of the target position defined relative to the mapping region by a user input.

Once the specification of the target position relative to the mapping region is activated, the target position can be changed by a change in location of the mapping region. In other words, the medical object can be guided by the relocation of the mapping region or via an input based on the image data. Once the specification of the target position relative to the mapping region is deactivated, on the other hand, the mapping region can be changed without a movement of the medical object being induced. This allows the imaging to be adjusted and/or defined target regions for the medical object to be approached independently of the mapping region.

According to one embodiment, the processing unit is designed in such a way that it determines a locational state of the mapping region in respect of the examination object and determines the one or more control signal(s) based on the locational state.

The locational state describes, in particular, the instantaneous location of the mapping region in respect of the examination object. The locational state can indicate, for example, the arrangement and/or position of the mapping region in the coordinates of the examination object or relative thereto. Furthermore, the locational state can indicate the arrangement and/or position of the mapping region relative to geometric anchor points of the examination object, such as for instance one or more organ(s) and/or anatomical landmark(s). The processing unit can be designed to determine the locational state based on a suitable location information. For this, the processing unit can be designed to receive the location information (for example from the imaging unit). For indication of the locational state in respect of the examination object, the processing unit can be designed to establish a registration between examination object and imaging unit.

The determination of the locational state of the mapping region relative to the examination object allows the specification of a target position by the imaging to be converted into precise instructions for the movement device. As a result of knowledge of the locational state of the mapping region relative to the examination object the movement of the medical object can be exactly matched to the examination object, so more complex movement patterns can be more easily specified for the medical object.

According to one embodiment, the processing unit is designed to receive information in respect of the examination object, which information includes information relating to a vessel structure of the examination object and/or information relating to a material property of the examination object and/or state information of the examination object. The processing unit is also designed to determine the one or more control signal(s) based on the information in respect of the examination object.

The information relating to a material property of the medical object can include, for example, a diameter and/or an elasticity and/or a density and/or deformability. The information relating to a vessel structure can be locally resolved based upon the examination object, in other words, describe local material properties of the examination object. The information relating to a vessel structure can include, for example, information on the course of vessels, on vessel diameters, vessel branchings, in particular bifurcations, and/or vessel curvatures and/or vessel anomalies. The state information of the examination object can include one or more physiological parameter(s) of the examination object that vary over time. The physiological parameters that vary over time can comprise the flow speed and/or the flow direction of a vessel fluid, for example blood, in a vessel structure. Alternatively or in addition, the parameters that change over time can comprise information in respect of a breathing cycle and/or cardiological data.

The information in respect of the examination object can be provided to the processing unit as a data set. The processing unit can be designed to receive the data set (for example to load or retrieve from a data memory inside the processing unit or via the data interface). In particular, the data set can at least partially map a vessel structure of an examination object.

The information in respect of the examination object (the data set) can be registered with the examination object and/or the imaging unit and/or the movement device.

Furthermore, the information in respect of the examination object can be provided by the imaging system. For example, one or more parameter(s) that vary over time can be determined by the imaging system. In particular, flow speed and flow direction can be determined by ultrasound-based imaging.

Actuation of the movement device can be optimized further by taking into account the additional information in respect of the examination object. In particular, it is conceivable that the one or more control signal(s) can be adjusted or optimized based upon the information in respect of the examination object. The specification of the target position by the location of the mapping region could then serve as a "rough" specification, which is adjusted further based upon the conditions inside the examination object.

According to one embodiment, when determining the one or more control signal(s) the processing unit is designed to determine a movement trajectory for the medical object (or the predefined section of the medical object), which is capable of moving the medical object (or the predefined section) in particular in the examination object from the instantaneous position to the target position. The processing unit is also designed, in particular, to determine the one or more control command(s) based on the movement trajectory (and/or transfer the movement trajectory into the one or more control command(s)).

The movement trajectory can have a sequence of space-time points and/or a space-time curve, which leads from the instantaneous position of the medical object (of the predefined section) in the examination object to the target position. The movement trajectory can be, in particular, two-dimensional and/or three-dimensional. For creation of the movement trajectory the processing unit can be designed, for example, to apply a trajectory planning algorithm. Advantageously, the processing unit can be designed to take into account the information in respect of the examination object.

Preferably, the movement device is designed to move the medical object, in particular a part of the medical object arranged in the examination object, also in particular the predefined section, along the movement trajectory. The movement device can be designed to move the medical object along the longitudinal extension direction of the medical object and/or around the longitudinal extension direction in such a way that the part of the medical object, which is arranged inside the examination object, in particular the vessel structure, follows the movement trajectory. The movement device can also be designed to deform and/or orient the tip of the medical object in a defined manner in such a way that, for example due to a rotational movement, this tip follows the movement trajectory. This can be helpful, in particular, with vessel branchings, for example a bifurcation and/or an orifice.

According to one embodiment, the processing unit is also designed to determine the movement trajectory based on the information in respect of the examination object (based on the data set).

As a result, in particular vessel structures can be taken into account in path planning for the medical object, and this makes control of the medical object safer.

According to one embodiment, the processing unit is designed to establish a registration between the imaging unit and the movement device when determining the one or more control signal(s). In other words, a coordinate system of the imaging unit can advantageously be registered with the coordinate system of the movement device. A corresponding spatial position in the coordinate system of the movement device can be assigned to each position in the mapping region hereby. In addition, the processing unit can be designed to establish a corresponding registration between the imaging unit and the examination object or between the examination object and the movement device.

The registrations mean position and location details can be easily converted into each other, and this can facilitate, for example, the output of suitable control commands for actuation of the movement device.

According to one embodiment, the imaging system or the intervention system also has a positioning device, which is designed for robotic positioning of the imaging unit relative to the examination object in such a way that the positioning device can robotically set the location of the mapping region in respect of the examination object.

The imaging system or the intervention system can be designed in such a way that the positioning device can be controlled via a user input. For this, the imaging system or the intervention system (the processing unit) can have a user interface, which is designed in such a way that a user input for control of the positioning device can be input into it. The processing unit can also be designed such that it actuates the positioning device based on the user input. A user interface suitable for this can be designed, for example, as a joystick. In addition or alternatively, the processing unit can be designed to automatically actuate the positioning unit, in other words, without dedicated user input.

In general, the positioning device makes more accurate setting and more precise retaining of the location of the mapping region relative to the examination object possible, and this unburdens the user when operating the imaging or intervention system. In addition, the positioning device optionally enables automatic tracking of the mapping region, for example relative to the medical object, and this can further improve the operator convenience. A suitable sensor system can ensure, for example, contact between the examination object and an ultrasonic head as part of the imaging system (for example via force feedback).

According to one embodiment, the positioning device can have a 6 DOF or 7 DOF robot, and in particular a 7 DOF lightweight robot. "DOF" designates the "Degrees of Freedom", in other words the degrees of freedom of movement of the robot used. The lightweight robot is preferably modular in design and, more preferably, a recreation of the human arm.

Robots of this kind enable increased flexibility and manipulability and are good for setting the location of the mapping region, therefore.

The positioning device can also have an integrated sensor system for the detection of external forces. The processing unit can be designed to control the positioning device based on the detected forces.

This can make it possible to yield to external forces on movement of the imaging unit and to carry out sensitive movements and complex motion sequences, as may be required, for example, on putting and moving an ultrasonic unit on the examination object. In addition, this can optionally ensure that the ultrasonic unit is in contact with the examination object.

According to one embodiment, the movement device is designed to provide the processing unit with movement information, from which movement information the movement state and, in particular, the instantaneous position of the medical object can be derived. The movement state of the medical object describes the instantaneous movement behavior of the medical object in respect of the locational state and/or the examination object so at least one instantaneous position of the predefined section in respect of the mapping region and/or of the examination object can be derived from the movement state. In other words, the movement state allows a conclusion about the arrangement of the medical object (of the predefined section) relative to the location of the mapping region or the examination object. The movement state can include, for example, information relating to a speed, in particular a movement speed, of the medical object (of the predefined section) relative to the mapping region (and therewith examination object). The information on the speed of the medical object (of the predefined section) can include information relating to a translational speed of the medical object along its longitudinal extension direction and/or information relating to a rotational speed of the medical object around its longitudinal extension direction.

Furthermore, the movement state can include an orientation and/or a relative position and/or movement distance of the medical object (of the predefined section) relative to the examination object and/or mapping region. The movement state allows, therefore at least the instantaneous position of the predefined section in the coordinate system of the mapping region and/or of the locational state and/or of the examination object to be followed and used for automatic (re- or new) positioning of the medical object (of the predefined section). The movement information can include information relating to a speed and/or orientation and/or relative position and/or movement distance of the medical object. The movement information can also include a relative movement of the medical object in respect of the movement device. Advantageously, the movement information can include information relating to the, in particular instantaneous, movement state of the medical object relative to the movement device. The processing unit can then be designed to determine the instantaneous position of the medical object based upon the movement information.

The movement device can have, for example, a sensor unit, which is designed for detection of a movement of the medical object relative to the movement device. The sensor unit can have, in particular an encoder, for example a wheel encoder and/or a roller encoder, and/or an optical sensor, for example a barcode scanner and/or a laser scanner and/or a camera, and/or an electromagnetic sensor. For example, the sensor unit can be arranged so as to be at least partially integrated in the movement element, in particular the at least one actuator element, and/or the cassette element, in particular the at least one transmission element.

Alternatively or in addition, the movement device can be designed to provide the movement information based upon a control parameter for controlling the at least one actuator element and/or the at least one transmission element. Furthermore, the sensor unit can be designed for providing the movement information to the processing unit. The sensor unit can be designed, in particular, for detection of the relative movement of the medical object by a detection of the medical object relative to the movement device. Alternatively or in addition, the sensor unit can be designed for detection of a movement and/or change in location of components of the movement device, which components are movement-coupled to the medical object, for example the at least one actuator element and/or the at least one transmission element. Advantageously, the movement device, in particular the sensor unit, can be designed to determine the, in particular instantaneous, relative position and/or orientation and/or movement distance in respect of a reference positioning of the medical object at a reference instant, in particular an earlier one.

Advantageously, the movement device, in particular the sensor unit, can be designed for detecting the reference positioning of the medical object when a predefined section of the medical object is arranged in initial region, in particular the entry point and/or the introducer sheath. In particular, the reference positioning can include information relating to the spatial position and/or orientation of the medical object, in particular of the predefined section. For example, the movement device, in particular the sensor unit, can be designed to detect a movement state of the medical object on the movement device and/or a state of the movement device, in particular of components of the movement device movement-coupled to the medical object, at the reference instant.

Furthermore, the movement device can be designed for detecting a change in the movement state of the medical object in respect of the reference positioning. Based on the detected change in the movement state of the medical object, the movement device can be designed to provide the movement information to the processing unit. For example, the processing unit can be designed to determine a movement distance of the medical object, in particular in the vessel structure of the examination object, between the reference positioning and the, in particular instantaneous, positioning of the medical object based on the detected change in the state of the medical object on the movement device. The movement distance can describe, in particular, a spatial distance between the reference positioning and the instantaneous positioning of the medical object along its longitudinal extension direction.

In particular, the longitudinal extension direction of the medical object can run in a spatially curved manner. Because, from the entry point, the medical object is arranged along the movement trajectory in the vessel structure, the processing unit can be designed for the determining the relative and/or absolute spatial positioning of the medical object, in particular of the predefined section.

Advantageously, this can enable an accurate determination of the, in particular relative and absolute, spatial positioning of the medical object, in particular of the predefined section, in the examination object. By providing the movement information by way of the movement device, a further sensor system and/or a derivation of the movement state from the acquired image data can also be dispensed with, and this can simplify the system and reduce computing effort. Advantageously, the movement information provided by the movement device can be registered with the examination object. Such a registration can take place, for example, via the entry point of the medical object into the examination object, from which entry point all movements of the medical object can be defined.

According to one embodiment, the imaging unit is designed to provide the processing unit with image data of the mapping region. The processing unit is designed to extract the instantaneous position, in particular using algorithms for identification of the medical object, from the image data.

In other words, the image data can then be understood as a form of "movement information" from which the movement state of the medical object in respect of the examination object can be derived. The algorithms can be based on artificial intelligence, in other words, have one or more trained function(s). A trained function maps an input value in accordance with a "learned" mapping rule onto an output value. In the present case, input values can be taken to mean image data from the mapping region while the output values are the coordinates of the medical object (of the predefined section). By way of example, the algorithms can have one or more neural network(s), in particular what are known as Convolutional Neural Networks.

The determination of the instantaneous position by image data enables efficient determination or checking of the instantaneous position, which can also work independently of the movement device used.

According to one embodiment, the location of the target position (with activated target position specification) is firmly specified relative to the mapping region.

For example, the target position can be assigned to the center of the mapping region. A firm specification of the target position relative to the mapping region means the target position (with activated target position specification) is determined, in other words, by the location of the mapping region. As a result, the target position relative to the examination object can be changed directly by a change in location of the mapping region. The movement device and therewith the medical object can be controlled by a relocation of the mapping region, therefore. With ultrasound-based imaging (see below) the medical object can thereby be controlled by a manually guided ultrasonic head. A dedicated user interface for control of the robotically guided medical object can optionally be dispensed with due to such direct control of the medical object. If the user arrives with the medical object at a bifurcation, for example, he can now choose the correct branch extremely elegantly and guide the medical object onwards. The orientation and advance or withdrawal take place completely automatically from the manual movement of the ultrasonic head, which is "translated" into the one or more control signal(s). Orientation and advance or withdrawal can alternatively also be triggered by operation of an input element. In particular, the input element can be a push button. In particular, the input element can be arranged on the ultrasonic head.

According to a further embodiment, the target position can alternatively be dynamically fixed via a user interface. For this, the imaging or intervention system (the processing unit) can have a user interface, which is designed in such a way that a user can fix the target position inside the mapping region, in particular based on the image data acquired from the mapping region, by way of a user input. The thus fixed target position can then be provided to the processing unit by the user interface. Preferably, the user interface is designed for the presentation of one or more view(s) (perspectives) of the mapping region. Preferably, the user interface is also designed such that the user can fix the defined position directly in at least one of the presented views, for example via a capacitive and/or resistive display or by activating a different suitable input element (for example by "mouse click").

In this embodiment too the user has the advantage that he fixes the target position intuitively based on the mapping region. With activated target position specification this, in particular image-based, user input can be converted directly into corresponding control signals for movement of the medical object. In addition, no re-orientation of the mapping region has to occur, so possible delays and blurring due to the re-orientation can be avoided.

According to one embodiment, the processing unit is designed to repeatedly determine the one or more control signal(s) (the movement trajectory) on a change in the locational state and/or target position relative to the locational state.

Repeated determination of the one or more control signal(s) (or optionally the movement trajectory) on a change in the instantaneous location of the mapping region and/or the target position means the position of the medical object can be constantly adjusted to the target position (if the target position specification is activated).

The movement trajectory can be repeatedly determined in particular as a function of a threshold value in respect of the change in the locational state and/or the target position. This has the advantage that small unspecific (and often also unintentional) changes, which can emanate, for example, from slight jolting in the system, or which develop with manual (by hand) guidance of the imaging unit, are not immediately converted into control commands for the movement device.

According to one embodiment, the imaging unit is also designed in such a way that the location of the mapping region can be set by a user manually and/or by a user input via a user interface, so the user can conveniently change the location of the mapping region and control the medical object, therefore.

According to one embodiment, the processing unit is also designed in such a way that it controls the imaging unit based on movement information, and in particular based on the instantaneous position of the medical object, and, more precisely, in particular to the extent that an optimization of the mapping of the mapping region is performed by adjusting one or more imaging parameter(s) of the imaging unit, and/or the location of the mapping region is adjusted in such a way that the medical object (or at least the predetermined section) is located in the mapping region.

The adjustment of the imaging unit as a function of the movement information/the instantaneous position means the imaging can be optimized. For this, imaging parameters of the imaging unit can be optimized. In the case of an ultrasonic unit, for example the orientation of the ultrasonic head, the Time-of-Flight window, the irradiation direction of the ultrasonic pulses, the irradiation width of the ultrasonic pulses, etc. can be adjusted to optimize the imaging. Furthermore, suitable mapping planes can be defined in the mapping region for an optimum presentation of the medical object. The optional setting of the location of the mapping region as a function of the instantaneous position of the medical object enables the medical object to be tracked, so it is possible to ensure, for example, that it remains in the field of vision of the user. If, in addition to the instantaneous position, further movement information, such as the advance speed of the medical object is also taken into account, an anticipatory relocation of the mapping region can also take place in the process.

According to one embodiment, the processing unit is designed in such a way that on control of the imaging unit it, in particular automatically, deactivates the specification of the target position defined relative to the mapping region based on the movement information/the instantaneous position. This can ensure that the optimization of the mapping region does not induce any undesirable movement of the medical object.

According to one embodiment, the processing unit can also be designed, in particular, in such a way that it actuates the positioning device based on the movement information in such a way that the predefined section of the medical object is located in the mapping region.

According to one embodiment, the imaging unit has an ultrasound imaging device with an ultrasonic unit, which ultrasonic unit is designed as an ultrasonic head for sonographic examination of the examination object.

The embodiment of the imaging unit as an ultrasound imaging device cooperates synergistically with inventive tracking of the medical object as a function of the imaging. The ultrasonic head may thus easily and intuitively move on the examination object, and, more precisely, both manually (in particular by hand) by way of the user and optionally robotically or with robotic assistance by way of the positioning device. An external, in particular manually guided, body ultrasonic head controls an introduced medical object thereby.

According to one embodiment, the positioning device is designed to set the positioning of the ultrasonic unit on the examination object in the respective location for acquisition of the mapping region. In particular, the positioning device is designed to set the positioning of the ultrasonic head on the examination object in accordance with a specified location. The specified location can be determined, for example, by the (appropriately designed) processing unit or be specified by a user.

The precision of the orientation of the mapping region can be increased and the user can be unburdened further by the guidance of the ultrasonic unit (or of the ultrasonic head) by the positioning device.

According to one embodiment, the imaging or intervention system also has a presentation unit, which is designed in such a way that it displays at least a first presentation of the mapping region. The presentation unit is also designed in such a way that it displays a marking overlaid on the first presentation, which marking indicates the target position in the first presentation.

The overlaid presentation of the mapping region and the marking renders the user capable of visually checking tracking of the medical object by way of a change in position of the imaging in real time. This enables intuitive and less error-prone operation. The first presentation can preferably be a side view of the long side of the medical object in the examination object (what is known as a long-axis view) or a cross-sectional view of the medical object substantially perpendicularly to the longitudinal direction (what is known as a short-axis view) or change over between the two views (long and short-axis views, therefore), in particular by way of a user input. The presentation unit is then designed in such a way that a corresponding user input can be input.

According to one embodiment, the presentation unit is also designed for display of a second presentation of the mapping region, with the perspective of the second presentation differing from the perspective of the first presentation. Furthermore, the presentation unit is designed for the display of a marking overlaid on the second presentation, which marking indicates the defined position in the second presentation.

In other words, the user is provided with at least two different perspectives of the intervention process, so he can better assess and control the spatial location of the medical object in the examination object. First and second presentations can be presented simultaneously (for example inside a graphical user interface). Alternatively, the presentation unit can be designed to change over between first and second presentation. The changeover can occur automatically, for example by way of a control signal of the processing unit. The processing unit can then be designed to provide the presentation unit with a corresponding control signal for changing over between the two presentations. The control signal can be based, in particular, on movement information or the movement state or the instantaneous location of the medical object. The automatic changeover can further improve the assistance to the user when carrying out the intervention. In particular, feedback on the movement state is thus possible. Alternatively or in addition, the presentation unit can be designed in such a way that it is possible to change over between first and second presentation by way of a user input. The presentation unit is then designed such that a corresponding user input can be input.

According to one embodiment, the processing unit is also designed in such a way that it outputs a warning message to a user via the data interface when the data link is interrupted, with the data interface being designed, in particular, as a wireless data interface.

The output of a warning message immediately informs the user if guidance of the medical object by way of the imaging unit is not instantaneously possible, and this further increases the safety of the procedure. A wireless data link can reduce the wiring effort, and this improves the modular properties of the system.

According to one embodiment, the processing unit is designed in such a way that it outputs the warning message by way of an optical and/or acoustic and/or haptic warning via a user interface to a user. If the imaging unit has an ultrasound device, the ultrasonic head can be designed to output the warning message as a haptic warning message, for example in the form of a vibration of the ultrasonic head.

According to a further embodiment, a method for control of an imaging or intervention system according to the aspects and embodiments is provided. The method has the following steps: acquiring image data of a mapping region inside the examination object via the imaging unit; determining an instantaneous position of the medical object; specifying a target position for the medical object, which target position is defined relative to the mapping region (in other words, is defined based upon the mapping region or based on the mapping region or is defined in specified relative location to the mapping region); determining one or more control signal(s) for the movement device, which one or more control signal(s) are capable of causing the movement device to move the medical object from the instantaneous position to the target position; providing the one or more control signal(s) to the movement device via the data interface.

Preferably, the method also includes the step of changing the location of the mapping region and subsequently repeating said method steps.

Preferably, the method also includes the step of determining a locational state of the mapping region in respect of the examination object, wherein the one or more control signal(s) are determined based upon the locational state.

The advantages of the proposed method for control of an intervention systems substantially correspond to the advantages of the proposed system. Features, advantages or alternative embodiments can likewise be transferred to the other claimed subject matters and vice versa.

In a further embodiment, the invention relates to a computer program product, which comprises a program and can be loaded directly into a memory of a programmable arithmetic unit and has program segments, for example libraries and help functions, in order to carry out a method for control of an intervention systems, in particular according to the embodiment, when the computer program product is executed. The computer program product can comprise software with a source code, which still has to be compiled and linked or which just has to be interpreted, or an executable software code, which just has to be loaded into the processing unit for execution. As a result of the computer program product, the method for control of a medical imaging device can be carried out quickly, in a manner that can be repeated identically and robustly.

The computer program product is configured such that it can perform an embodiment of the inventive method steps by way of the processing unit. The processing unit has in each case to exhibit the prerequisites such as, for example, an appropriate main memory, an appropriate graphics card or an appropriate logic unit, so the respective method steps can be performed efficiently.

In an embodiment, the computer program product is stored, for example, on a computer-readable medium or stored on a network or server from where it can be loaded into the processor of a processing unit, which can be directly connected to the processing unit or be designed as part of the processing unit. Furthermore, control information of the computer program product can be stored on an electronically readable data carrier. The control information of the electronically readable data carrier can be configured in such a way that it carries out an embodiment of the inventive method when the data carrier is used in a processing unit. Examples of electronically readable data carriers are a DVD, a magnetic tape or a USB stick on which electronically readable control information, in particular software, is stored. When this control information is read from the data carrier and stored in a processing unit, all inventive embodiments of the above-described methods can be carried out. At least one embodiment of the invention can thus also start from said computer-readable medium and/or said electronically readable data carrier. The advantages of the proposed computer program product substantially correspond to the advantages of the proposed method.

FIG. 1 shows a schematic presentation of an advantageous embodiment of an imaging or intervention system 1 (also called "system" hereinafter).

As shown in FIG. 1, the system 1 can have an imaging unit 20 and a processing unit 22. In addition, the system 1 has a movement device CR, which is designed in such a way that it can position a medical object MD robotically in particular inside an examination object 31 and relative thereto. Processing unit 22 and movement device CR are connected via a data interface 35.

The examination object 31 can be regarded as a three-dimensional anatomical body with a plurality of cavities, on which an interventional procedure is to be carried out via the medical object MD. In particular, the examination object 31 can be a patient. Advantageously, the examination object 31 can be arranged on and/or at a patient supporting device 32. The patient supporting device 32 can be at least partially movable. The patient supporting device 32 can be designed, for example, as a surgical table. Advantageously, the patient supporting device 32 can have a movement device BV, which movement device BV can be controlled via a signal 28 from the processing unit 22 and/or the operating element C11.

The medical object MD can be designed as an, in particular elongate, therapeutic or surgical instrument and/or diagnostic instrument. In particular, the medical object MD can be flexible and/or mechanically deformable. The medical object MD can have, in particular at its distal end, an actuator, which is designed for the performance of a therapeutic or surgical and/or diagnostic task inside the examination object 31. The medical object MD can be designed, for example, as a catheter and/or endoscope and/or guide wire and/or tissue manipulator. The movement device CR can be designed for positioning and/or remote manipulation of the actuator. For example, the movement device CR can be designed as a catheter robot, minimally invasive surgical robot, endoscopy robot, etc. Furthermore, the movement device CR can be designed for movement of the medical object MD along a predefined movement trajectory. Advantageously, the medical object MD can be introduced via an introducer sheath at an entry point IP into the examination object 31, for example into a vessel or organ structure of the examination object 31. The medical object can have a predefined section VD. This can have the actuator, a tip of the medical object, a marker structure for improved visibility in the imaging, or another section of the medical object MD.

The movement device CR can be fastened, in particular movably, via a fastening element 71, for example a stand and/or robotic arm, to the patient supporting device 32. Advantageously, the movement device CR can be designed to move the medical object MD arranged therein in a translational manner at least along a longitudinal extension direction of the medical object. Furthermore, the movement device CR can be designed to rotate the medical object MD around the longitudinal extension direction. Alternatively or in addition, the movement device CR can be designed to control a movement of at least part of the medical object MD, in particular at a distal end of the medical object MD, in particular in the form of the actuator. The movement device CR can be designed, in particular, in such a way that it can be actuated for positioning of the medical object MD via a control signal from the processing unit 22 via the data interface 35. Conversely, the movement device CR can also be designed for providing information in respect of a movement or positioning state (movement information) of the medical object MD (and in particular of the actuator) to the processing unit 22 via the data interface 35.

According to the present embodiment, the imaging unit 20 is designed as an ultrasound imaging system. As such, the imaging unit 20 can have an ultrasonic unit US, which can be designed as an ultrasonic head or ultrasonic probe. The ultrasonic unit US can in general have one or more ultrasonic transmitter(s) and one or more ultrasonic sensor(s). The ultrasonic transmitters are designed for the emission of ultrasound into the examination object 31. The ultrasonic sensors detect the ultrasonic signals coming back from the examination object 31 and optionally the medical object introduced therein. Time-of-Flight measurements can enable a three-dimensional presentation. The region mapped in the process (mapping region AB) is defined partially by the position of the ultrasonic unit US on the examination object 31 and partially by one or more imaging parameter(s) of the ultrasonic unit US. Thus, for example, the spatial radiation width, the propagation angle and/or the propagation directions of the ultrasonic pulses can be changed. Furthermore, for example, one or more mapping plane(s) can be defined, from which ultrasonic signals are evaluated. Conventionally, at least two intersecting mapping planes are defined, which enable a perspective along the medical object (in other words along the longitudinal extension direction; what is known as the long-axis view, LAV, cf. FIG. 2) and a perspective perpendicular to the longitudinal extension direction of the medical object in which the medical object then appears more or less punctiform (what is known as the short-axis view, SAV; cf. FIG. 2). Furthermore, more than two mapping planes can also be fixed, and this can further support the simultaneous presentation of the medical object MD and the surrounding part of the examination object 31.

The imaging unit 20 can be set in such a way that the ultrasonic unit US maps a fixed region inside the examination object 31, the mapping region AB. The mapping region AB has a fixed locational state (or instantaneous location) relative to the examination object 31, which depends on the position of the ultrasonic unit US and the imaging parameters. The imaging unit 20 is also designed in such a way that the locational state of the mapping region AB is changeable—for instance by adjusting the imaging parameter or by a change in position of the ultrasonic unit US. Actuation signals for setting the locational state can be transmitted, for example from the processing unit 22 via a suitable data interface 36. Actuation signals can be based on a user input, which user inputs this into the system 1 via a user interface 41, 42, for example in the form of a joystick, touchpad, a mouse or keyboard. Alternatively, actuation signals can also be automatically generated by the processing unit 22 without user specification.

The positioning of the ultrasonic unit US can be carried out by a user by hand. A fine adjustment of the locational state can then occur by adjustment of the imaging parameter. Furthermore, the imaging unit 20 can have a positioning device 21, which is designed for, preferably robotic, positioning and/or movement of the ultrasonic unit US in particular on the examination object 31. The positioning device 21 can be controlled by control signals, which are transmitted to the positioning device 21 from the processing unit 22 via the data interface 36. Conversely, the imaging unit 20 can provide the processing unit 22 with location information in respect of the locational state via the data interface 36. This location information can include said imaging parameters, which have image data per se and positioning parameters from the positioning device 21.

By way of example, the positioning device 21 can be designed as a 6 DOF (Degrees Of Freedom) or a 7 DOF robot. In the preferred embodiment, what is known as a lightweight robot (LBR) is used, which is preferably modular in design and is a recreation of the human arm. Robots of this kind have up to seven degrees of freedom and compared to conventional industrial robots enable increased flexibility and manipulability. An integrated sensor system in conjunction with suitable control algorithms make it possible to yield to external forces and carry out sensitive movements and complex motion sequences, as may be necessary, for example, on putting the ultrasonic unit US on the examination object 31. The sensor system also enables the determination of positioning parameters for transmission to the processing unit 22. As shown in FIG. 1, the positioning device 21 can be fastened, in particular movably, to the patient supporting device 32. Alternatively, the positioning device 21 can be provided separately from the patient supporting device 32 and have, for example, its own stand.

Alternatively or in addition, the imaging unit 20 can also have one or more medical imaging device(s) differing from an ultrasonic imaging system. For example, the imaging unit 20 can have a medical C-arm X-ray apparatus with a detector unit and an X-ray source. For acquisition of the image data and setting a defined locational state of the mapped region relative to the examination object 31 the arm of the medical C-arm X-ray apparatus can be mounted to be movable around one or more axes. Furthermore, the medical C-arm X-ray apparatus can comprise a positioning device, which enables a movement of the medical C-arm X-ray apparatus in the space. According to an example embodiment, the imaging unit 20 can have an ultrasonic imaging system and a C-arm X-ray apparatus.

The processing unit 22 can also have a user interface 41, 42. The user interface 41, 42 can have an input element 42, for example a keyboard, and/or a presentation unit 41, for example a monitor and/or display. The input element 42 can be integrated in the presentation unit 41, for example in the form of a capacitive and/or resistive input display. A user input at the input element 42 enables, in particular supplementary, control of the imaging unit 20 (the positioning unit 21) and/or the movement device CR and/or the patient supporting device 32. For this, the input element 42 can send, for example, a signal to the processing unit 22 via a corresponding data interface 26.

Furthermore, the presentation unit 41 can be designed to display information and/or graphical presentations of information, in particular image data, of the imaging unit 20 for example in a graphical user interface GUI. For this, the processing unit 22 can send a control signal to the presentation unit 41, for example via a data interface 25.

The different components of the intervention system 1 can be coordinated by the processing unit 22. A data exchange is ensured via the data interfaces 25, 26, 35, 36. The processing unit 22 can be designed as a central control unit, for example as a control device with one or more processor(s). Alternatively, the processing unit 22 can be designed as part of the imaging unit 20 or the movement device CR. As a further embodiment the functionalities of the processing unit 22 described below can also be decentrally distributed among a plurality of arithmetic units or control devices.

According to one embodiment, the processing unit 22 is also designed in such a way as to monitor the connection between the components via the data interfaces 25, 26, 35 and 36 of the intervention system 1 and to output a warning message to a user if the connection is interrupted or faulty. The warning message can be output, for example, as an optical and/or acoustic warning message, in particular by the presentation unit 41. Alternatively or in addition, the warning message can also be configured as a haptic warning message for the user. In particular, the input element 42 can be designed to output a haptic warning message, for instance by impressing a vibration on the input element 42. An ultrasonic head can also be designed in such a way that it makes a warning message haptically perceptible, for example by triggering a vibration of the ultrasonic head.

Generally, the processing unit 22 is designed in such a way that it controls a movement of the medical object MD based on the locational state of the mapping region AB. This enables, for example, tracking of the medical object MD with the imaging, or navigating of the medical object MD by way of a purposeful change in the locational state of the mapping region AB. In other words, it is thus possible for a user to control a movement of the medical object by a movement of the ultrasonic unit US, which occurs either by hand or in a robot-assisted manner. Robot-assisted can comprise fully automatic or semi-automatic movement. A semi-automatic movement control can include, for example, just robotically supporting the weight of the ultrasonic unit US, so the user can move the ultrasonic unit US with minimal force (what is known as "Zero Gravity Mode"). Navigating of the medical object MD can take place such that the predefined section VD of the medical object MD is moved to a target position TP in the examination object 31.

Conversely (or in addition), the processing unit 22 can also be designed in such a way that it controls the locational state of the mapping region AB based on the movement state of the medical object MD and thus the imaging tracks the medical object MD. In other words, the processing unit 22 can be designed to control, at least as a function of the instantaneous position of the medical object MD, a locational state of the mapping region AB such that the predefined section VD of the medical object MD is included in the mapping region AB and can thus be mapped by use of the image data acquired by the imaging unit 20. The locational state can preferably be adjusted via the positioning device 21.

For reciprocal control of the locational state of the mapped region AB as a function of the movement state of the medical object MD the processing unit 22 can be designed to determine (or calculate) the locational and movement states (or the instantaneous position of the medical object MD) from the available basic information. Basic information on the determination of the locational state will also be referred to as location information hereinafter; basic information on the determination of the movement state (at least the instantaneous position of the medical object MD) as movement information. The processing unit 22 can also be set up in such a way that it obtains such basic information from the components of the system 1 and processes it accordingly. For this, the processing unit 22 can be connected, for example, to the imaging unit 20 and/or the movement device CR in a wired manner or wirelessly via data interfaces 35, 36.

The processing unit 22 can thus obtain location information, for example from the imaging unit 20, from which the locational state of the mapping region AB in respect of the examination object 31 may be determined. For example, this location information can comprise one or more imaging parameter(s), which describe(s), for example, the setting of the ultrasonic transmitter and ultrasonic receiver of the ultrasonic unit US. As an alternative or in addition, the location information can comprise one or more positioning parameter(s), which define the position of the ultrasonic unit US. For example, the positioning parameters can include a speed and/or orientation and/or relative position and/or movement distance of the ultrasonic unit US in respect of the examination object 31. The positioning parameters can be provided by the positioning unit 21. Alternatively, the location information can be determined by triangulation. For this, for example, one or more tracking probe(s) can be arranged on the ultrasonic unit US, which tracking probes emit measurement signals, which are dependent on a position relative to a predefined reference point. The tracking probes can be designed, for example, as coil elements whose measurement signals depend on their respective position in an electromagnetic field, which is generated by a suitable field generation unit. Advantageously, three coil elements are used in an embodiment of this kind in order to adequately detect all degrees of freedom of movement. Furthermore, image data from the mapping region AB can also include location information. The processing unit 22 can be designed in such a way that it determines the locational state of the mapping region AB in respect of the examination object 31 from image data by image processing. For this, the processing unit 22 can make use, for example, of algorithms, which detect anatomical landmarks in medical image data, so the mapping region AB may be linked to the coordinate system of the examination object 31. According to one advantageous embodiment, one or more trained function(s) can be used here, for example in the form of one or more neural network(s), which were trained for the detection of anatomical landmarks in (ultrasound) image data. The processing unit 22 can be designed in such a way that it determines a locational state of the mapping region AB in respect of the examination object 31 based upon one or more item(s) of said location information.

The processing unit 22 can obtain movement information from the movement device CR. Movement information can comprise, for example, one or more movement parameter(s), which define the movement state of the medical object MD. For example, the movement parameters can include a speed and/or orientation and/or relative position and/or movement distance of the medical object MD (in particular of the predefined section VD). Alternatively or in addition, the processing unit 22 can obtain movement information in the form of image data via the imaging unit 20. The movement state of the medical object MD can then be determined by evaluation of the image data from the mapping region AB. For this, the processing unit 22 can make use, for example, of algorithms, which identify the medical object MD in the image data. According to one advantageous embodiment, one or more trained function(s), for example in the form of one or more neural network(s), can be used, which were trained for the detection of medical objects MD in (ultrasound) image data. To increase the visibility of the medical object MD in the image data, the ultrasonic signature in particular of the predefined section VD can be increased by suitable coatings and geometries and/or by marker structures. The use of active ultrasonic transmitters on the medical object MD for locating the same is also possible. Furthermore, movement information can also be obtained by the use of said tracking sensors on the medical object MD and be provided to the processing unit 22.

In order to control the movement state, and in particular the position of the medical object MD, based on the locational state of the mapping region AB the processing unit 22 can also be designed such that it registers the imaging unit 20 with the movement device CR and thus establishes a registration between the locational and movement states. The registration is a procedure, which links the coordinate system of the imaging unit 20 to that of the movement device CR. This can occur via a shared coordinate system (for example, the coordinate system of the examination object 31 can act as such a shared coordinate system). The registration can then convert, for example, a change in location of the mapping region AB or the specification of a target position TP inside the mapping region AB into an instruction for a change in position of the medical object MD in the examination object 31 (since the locational state is defined relative to the examination object 31). The registration can take place, for example, based upon a calibrated initial state for which the relationship between the coordinate systems is known. Locational state and movement state can then be detected as changes with respect to such a calibrated initial state. Alternatively an image-based registration is conceivable, with locational and movement states being defined, for example, relative to anatomical landmarks of the examination object 31. Furthermore, the relative relationship between locational and movement states and a registration can also be achieved by evaluation of tracking sensors on the imaging unit 20 and/or the medical object M, therefore. A combination of said registration methods is also possible.

Figure 2:
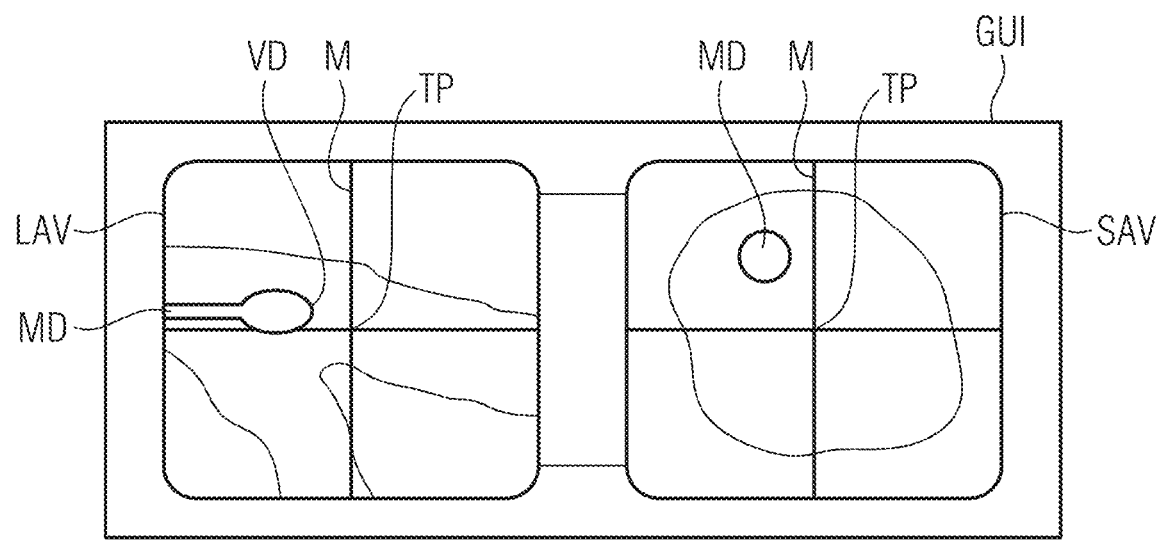
FIG. 2 shows a schematic presentation of a graphical user interface (Graphical User Interface) according to one embodiment.

FIG. 2 shows example presentation forms of the information presented by the presentation unit 41. Preferably, the information is presented in a graphical user interface GUI. Preferably, the processing unit 22 and the presentation unit 41 are designed such that they present at least two different presentations LAV, SAV of the mapping region AB, which presentations LAV, SAV show, in particular, different perspectives of the mapping region AB. As shown in FIG. 2, one of these presentations can be a longitudinal view along the longitudinal extension direction of the medical object MD (long-axis view, LAV), while the other presentation corresponds to a perspective with viewing direction parallel to the longitudinal extension direction of the medical object MD (short-axis view SAV). While the long-axis view LAV allows the user to estimate the position of the medical object MD in the advance direction, the short-axis view SAV is suitable for checking the position of the medical object MD transversely to the advance direction. As an alternative to the simultaneous presentation of a plurality of presentations LAV, SAV shown in FIG. 2, the processing unit 22 and the presentation unit 41 can also be designed to automatically change over, or change over in response to a user input, between different presentations LAV, SAV, in particular between the long-axis view LAV and the short-axis view SAV.

Processing unit 22 and presentation unit 41 can also be designed such that they display the target position TP for the medical object MD inside the mapping region AB. The target position TP can be presented by a marking M. The marking M can be overlaid on the presented image data, for example, as shown in FIG. 2, as a type of crosshairs. The target position TP can be firmly specified in respect of the mapping region AB. For example, the target position TP can be fixed in the center of the mapping region AB. The target position TP can then be set relative to the examination object 31 by changing the locational state of the mapping region AB in respect of the examination object 31. In other words, by moving the imaging unit 20 the target position TP can be changed in respect of the examination object 31. The change can take place by manual guiding of the ultrasonic unit US or in a robot-assisted manner by the positioning device 21. The commands for robotic setting of the locational state can be specified by a user via the input element 42. To enable three-dimensional guiding, processing unit 22 and presentation unit 41 can also be designed in such a way that the user can choose between a plurality of complementary perspectives LAV, SAV for navigation of the target position TP. In the long-axis view LAV, for example, the advance along the medical object MD can thus be controlled while the short-axis view SAV allows positioning laterally thereto. The user inputs for navigation of the target position TP then relate in each case to the currently selected perspective SAV or LAV.

In addition or as an alternative, processing unit 22 and presentation unit 41 can also be designed in such a way that the user can flexibly set the target position TP in the mapping region AB. For this, the user can mark, for example via the input element 42, a point in the mapping region AB or the presented perspectives LAV, SAV, for instance by mouse click or touching a capacitive and/or resistive display.

Since the locational state of the mapping region AB relative to the examination object 31 is known, the position of the target position TP in respect of the examination object 31 is also known. This accordingly allows a movement trajectory to be determined, which guides the medical object MD to the target position TP.

The processing unit 22 can also be designed to control a movement of the patient supporting device 32 in such a way that the imaging unit 20 is appropriately positioned relative to the examination object 31.

Figure 3:
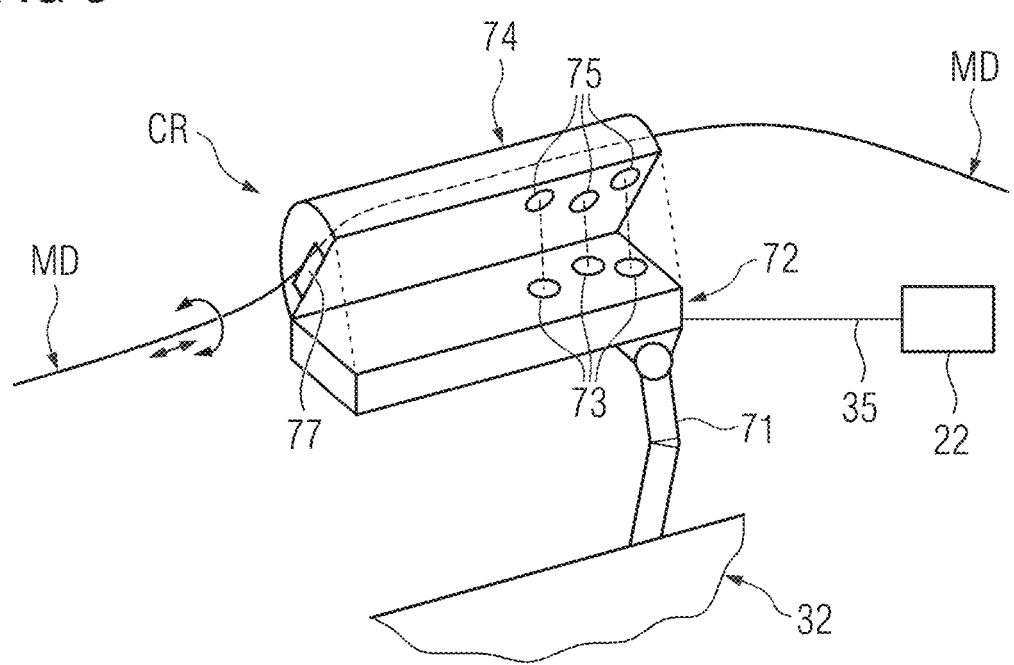
FIG. 3 shows a schematic presentation of a movement device for robotic movement of a medical object.

FIG. 3 shows a schematic presentation of a movement device CR for robotic movement of a medical object MD according to one embodiment. Advantageously, the movement device CR can have a fastening element 71, in a particular a movable and/or displaceable one. Furthermore, the movement device CR can have a cassette element 74, which is designed for receiving at least part of the medical object MD. Furthermore, the movement device CR can have a movement element 72, which is fastened to the fastening element 71, for example a stand and/or robotic arm. In addition, the fastening element 71 can be designed to fasten the movement element 72 to the patient supporting device 32, in particular movably. Furthermore, the movement element 72 can advantageously have at least one, for example three, actuator element(s) 73, for example an electric motor, with the processing unit 22 being designed for controlling the at least one actuator element 73. Advantageously, the cassette element 74 can be coupled, in particular mechanically and/or electromagnetically and/or pneumatically, to the movement element 72, in particular the at least one actuator element 73. The cassette element 74 can also have at least one transmission element 75, which can be moved by way of the coupling between the cassette element 74 and the movement element 72, in particular the at least one actuator element 73. In particular, the at least one transmission element 75 can be movement-coupled to the at least one actuator element 73. Furthermore, the transmission element 75 can be designed to transmit a movement of the actuator element 73 to the medical object MD in such a way that the medical object MD is moved along a longitudinal extension direction of the medical object MD and/or that the medical object MD is rotated around the longitudinal extension direction. The at least one transmission element 75 can have, for example, a pulley and/or roller and/or slit.

Advantageously, the movement element 72 can have a plurality of, in particular independently controllable, movement elements 73. Furthermore, the cassette element 74 can have a plurality of transmission elements 75, in particular at least one movement-coupled transmission element 75 for each of the movement elements 73. This can enable, in particular independent and/or simultaneous, movement of the medical object MD along different degrees of freedom of movement.

Furthermore, the movement device CR, in particular the at least one actuator element 73, can be controlled via the signal 35 from the processing unit 22. The movement of the medical object MD can be controlled, in particular indirectly, by the processing unit 22 hereby. In addition, an orientation and/or position of the movement device CR relative to the examination object 31 can be adjusted by a movement of the fastening element 71. Advantageously, the movement device CR is designed for providing movement information to the processing unit 22.

For this, the movement device CR can have, for example, a sensor unit 77, which is designed for detection of a movement of the medical object MD relative to the movement device CR. The sensor unit 77 can have, in particular, an encoder, for example a wheel encoder and/or a roller encoder, and/or an optical sensor, for example a barcode scanner and/or a laser scanner and/or a camera, and/or an electromagnetic sensor. For example, the sensor unit 77 can be arranged so as to be at least partially integrated in the movement element 72, in particular the at least one actuator element 73, and/or the cassette element 74, in particular the at least one transmission element 75. Alternatively or in addition, the movement device CR can be designed to provide the movement information based on a control parameter for controlling the at least one actuator element 73 and/or the at least one transmission element 74. Furthermore, the sensor unit 77 can be designed for providing the movement information to the processing unit 22. The sensor unit can be designed, in particular, for detection of the relative movement of the medical object MD by a detection of the medical object MD relative to the movement device. Alternatively or in addition, the sensor unit 77 can be designed for detection of a movement and/or change in location of components of the movement device CR, which components are movement-coupled to the medical object MD, for example the at least one actuator element 73 and/or the at least one transmission element 74.

The movement device CR can be designed, in particular, to provide the movement information including information relating to a speed and/or orientation and/or relative position and/or movement distance of the medical object MD. Furthermore, the processing unit 22 can be designed to repeatedly determine the positioning of the medical imaging device on a change in the movement information, in particular as a function of a threshold value in respect of the change in the movement information. A change in the movement information can describe a change in the position and/or orientation of the predefined section VD of the medical object MD in the examination object 31, for example in a vessel structure.

Figure 4:
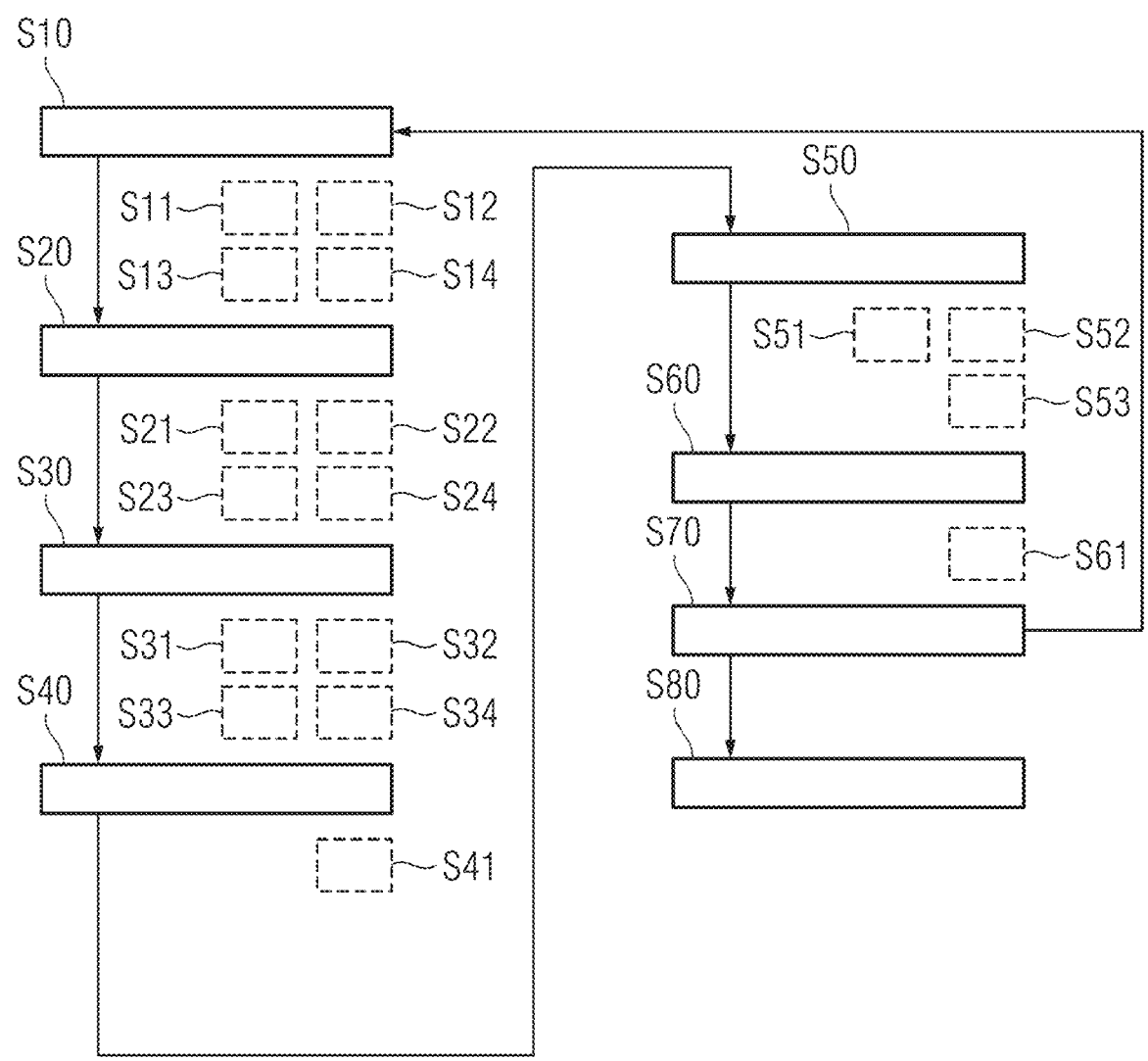
FIG. 4 shows a schematic presentation of an embodiment of the proposed method for control of a medical imaging device.

FIG. 4 shows a schematic presentation of an embodiment of the proposed method for control of the intervention systems 1. The order of method steps is not limited by either the presented sequence or by the chosen numbering. The order of steps can optionally be swapped and individual steps can be omitted.

A first step S10 is directed toward the acquisition of image data from mapping region AB with imaging unit 20. In an optional step S11, starting from the image data one or more presentation(s) LAV, SAV can be created, which can be output to a user via the presentation unit 41 in an optional step S12. In a further optional sub-step S13, a user input can be received so as to change over the output between different presentations LAV, SAV, whereupon the output can be changed between the different presentations in a further optional sub-step S14.

Step S20 is directed toward determining the locational state of the mapping region AB in respect of the examination object 31. Location information can be provided (optional sub-step S21) for determination of the locational state. The location information can be provided, for example, by the imaging unit 20 in the form of image data of the mapping region AB and/or positioning parameters of the imaging unit 20. In a further optional sub-step S22, this location information can be received by the processing unit 22. Alternatively, the location information can be provided in sub-step S21 by the processing unit 22 itself, for instance in the form of tracking data of one or more tracking sensor(s) suitably attached to the imaging unit 20 or results of an evaluation of image data of the mapping region AB. In a further optional sub-step S23, the locational state of the mapping region AB is calculated (by the appropriately designed processing unit 22) from the location information. In a further optional sub-step S24, the location information and or the locational state can be registered with the coordinate system of the examination object 31.

In step S30, the movement state of the medical object MD is determined relative to the examination object 31. In particular, the instantaneous position of the medical object MD (of the predefined section VD) can be determined. For this, movement information of the medical object MD can be provided in an optional sub-step S31, for example as movement parameters, by the movement device CR or in the form of image data of the mapping region AB by the imaging unit 20. In a further optional sub-step S32, this movement information can be received by the processing unit 22. Alternatively, the movement information can be provided in sub-step S31 by the processing unit 22 itself, for instance in the form of tracking data of one or more tracking sensor(s) suitably attached to the movement device CR and/or the medical object MD or as a result of an evaluation of image data of the mapping region AB. In a further optional sub-step S33, the movement state of the medical object MD is calculated (by the appropriately designed processing unit 22) from the movement information. In a further optional sub-step S34, the movement information and/or the movement state can be registered with the coordinate system of the examination object 31 and or the locational state.

In step S40, a target position TP is specified for the medical object MD (the predetermined section VD) in respect of the examination object 31. The target position TP can have a specified positional relationship to the mapping region AB. The target position TP is then implicitly specified by the locational state of the mapping region AB. Alternatively, the defined position can be dynamically fixed in the mapping region AB in an optional sub-step S41 by a user input. The specification of the target position TP defined relative to the mapping region can be activated and/or deactivated.

In step S50, one or more control signal(s) are determined for the movement device, which are capable of moving the medical object MD (the predefined section VD) based on the movement state thereof to the target position TP. In particular, the one or more control signal(s) can be capable of moving the medical object MD (the predefined section VD) from the instantaneous position to the target position TP. In an optional sub-step S51, a movement trajectory can be determined, which is capable of moving the medical object MD (the predefined section VD) based on the movement state from the instantaneous position to the target position TP, based upon which movement trajectory the one or more control signal(s) can then be determined. In a further optional sub-step S52, additional information in respect of the examination object 31 can be taken into account on determination of the movement trajectory. Such additional information can be in the form, for example, of two-dimensional and/or three-dimensional and/or four-dimensional data sets, in particular image data sets, which are registered with the mapping region AB and are provided in a further optional sub-step S53.

In step S60, the one or more control signal (s) are provided to the movement device CR. In an optional sub-step S61, the medical object MD is moved by the movement device CR based upon (according to) the one or more control signal(s) (to the) target position TP).

In an optional step S70, a change in the location of the mapping region AB and/or the defined position is made by a user, whereupon processing repeats steps S10 to S60 (optionally including one or more optional sub-step(s)).

In an optional step S80, the imaging unit 20 is adjusted based upon the movement state (the instantaneous position) of the medical object MD, in order, for example, for the mapping region AB to track the medical object and/or to optimize the imaging to the movement state (the instantaneous position). Step S80 can be based, in particular, on the image data acquired in step S10.

The schematic presentations contained in the described figures do not depict any kind of scale or size ratios.

In conclusion, reference is made once again to the fact that the methods described in detail above and the illustrated devices are merely example embodiments, which can be modified in a wide variety of ways by a person skilled in the art without departing from the scope of the invention.

Furthermore, use of the indefinite article "a" or "an" does not preclude the relevant features from also being present several times. Similarly, the terms "unit" and "element" do not preclude the relevant components from consisting of a plurality of cooperating sub-components, which can optionally also be spatially distributed.

The following points are likewise part of the disclosure:
1. A medical imaging system with:
    a medical imaging unit (20) for mapping a mapping region (AB) inside an examination object (31), wherein the imaging unit (20) is designed in such a way that the location of the mapping region (AB) can be changed in respect of the examination object (31); and
    a processing unit (22), which has a data interface (35) to a movement device (CR) for robotic positioning of a medical object (MD) inside the examination object (31);
wherein:
    the processing unit (22) is designed in such a way that it determines an instantaneous position of the medical object (MD);
    the processing unit (22) is also designed in such a way that it specifies a target position (TP) for the medical object (MD);
    the processing unit (22) is also designed in such a way as to determine one or more control signal(s), which are capable of causing a movement of the medical object (MD) by way of the movement device (CR) from the instantaneous position to the target position (TP);
    the processing unit (22) is also designed to provide the one or more control signal(s) via the data interface (35) to the movement device (CR);
    the processing unit (22) is also designed in such a way that it tracks the target position (TP) of the location of the mapping region (AB).
2. The imaging system as claimed in 1, wherein the processing unit (22) is designed in such a way that the tracking of the target position (TP) can be activated and/or deactivated, in particular by a user input.
3. The imaging system as claimed in one of the preceding points, wherein the processing unit (22) is also designed in such a way that, that it:
    determines a locational state of the mapping region (AB) in respect of the examination object (31); and
    tracks the target position (TP) based on the locational state.
4. The imaging system as claimed in one of the preceding points, wherein the imaging unit (20) is also designed in such a way that the location of the mapping region (AB) can be set by a user manually, in particular by hand.
5. The imaging system as claimed in one of the preceding point, wherein
    the imaging unit (20) also has a positioning device (21), which is designed in such a way that it can robotically set the location of the mapping region (AB) in respect of the examination object (31).
6. The intervention system (1) with:
    a movement device (CR) for robotic positioning of a medical object (MD) inside an examination object (31) and relative thereto;
    a medical imaging unit (20) having an ultrasonic unit (US) for mapping a mapping region (AB) inside the examination object (31) by way of sonography;
    a positioning device (21) for robotic positioning of the ultrasonic unit (US) relative to the examination object (31); and
    a processing unit (22);
wherein:
    the processing unit (22) is designed in such a way that it determines an instantaneous position of the medical object (MD);
    the processing unit (22) is designed in such a way that it controls the positioning device (21) based on the movement state in such a way that the predefined section (VD) of the medical object (MD) is located in the mapping region (AB).
7. The intervention system as claimed in 5 or 6, wherein the positioning device has a 6 DOF or 7 DOF robot, in particular a 7 DOF lightweight robot.
8. The intervention system as claimed in 6 or 7, wherein:
    the movement device (CR) is designed to provide the processing unit (22) with movement information from which the instantaneous position of the medical object (MD) can be derived; and
    the processing unit (22) is designed to determine the instantaneous position of the medical object (MD) based on the movement information;
    wherein the movement information preferably includes information relating to a speed and/or orientation and/or relative position and/or movement distance of the medical object (MD).

Finally, it should again be noted that the devices and methods described above in detail are merely example embodiments which can be modified by a person skilled in the art in a wide variety of ways without departing from the scope of the invention. Furthermore, the use of the indefinite article "a" or "an" does not preclude the possibility that the relevant features can also be present plurally. Similarly, the expression "unit" does not preclude this including a plurality of components which can possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging system, comprising:
   a medical imaging device configured to map an imaged area inside an examination object, the medical imaging device being configured for changing a location of the imaged area in respect of the examination object by one of
      changing a position of the medical imagine device, or
      changing an imaging parameter of the medical imaging device; and
   a processing device configured to robotically position a medical object inside the examination object via a movement device, the processing device being configured to
      determine an instantaneous position of the medical object,
      specify a target position for the medical object, the target position being defined relative to the imaged area,
      determine one or more control signals based on a change in the location of the imaged area, the one or more control signals being configured to cause a movement of the medical object via the movement device from the instantaneous position to the target position, and
      provide the one or more control signals to the movement device.

2. The medical imaging system of claim 1, wherein the processing device is configured to:
   perform the specification of the target position based on the specification being activated; and
   deactivate a functionality for specifying the target positon.

3. The medical imaging system of claim 2, wherein the processing device is configured to firmly specify the target position relative to the imaged area.

4. The medical imaging system of claim 2, further comprising:
   a user interface configured to receive an input from an external source specifying the target position inside the imaged area.

5. The medical imaging system of claim 2, wherein the processing device is configured to:
   determine a locational state of the imaged area of the examination object; and
   determine the one or more control signals based upon the locational state.

6. The medical imaging system of claim 5, wherein
   the medical imaging device is configured to provide location information, the location information including at least one of
      information regarding at least one of one of a speed, orientation, relative position or movement distance of at least one imaging component of the medical imaging device, and
      image data of the imaged area; and
   the processing device is configured to determine the locational state based on the location information.

7. The medical imaging system of claim 1, wherein the processing device is configured to firmly specify s the target position relative to the imaged area.

8. The medical imaging system of claim 7, wherein the processing device is configured to:
   determine a locational state of the imaged area of the examination object; and
   determine the one or more control signals based upon the locational state.

9. The medical imaging system of claim 8, wherein
   the medical imaging device is designed to provide location information, the location information including at least one of
      information regarding at least one of one of a speed, orientation, relative position or movement distance of at least one imaging component of the medical imaging device, and
      image data of the imaged area; and
   the processing device is configured to determine the locational state based on the location information.

10. The medical imaging system of claim 1, further comprising:
    a user interface configured to receive an input from an external source specifying the target position inside the imaged area.

11. The medical imaging system of claim 1, wherein the processing device is configured to:
    determine a locational state of the imaged area with respect to the examination object; and
    determine the one or more control signals based upon the locational state.

12. The medical imaging system of claim 11, wherein
    the medical imaging device is configured to provide location information, the location information including at least one of
       information regarding at least one of a speed, orientation, relative position or movement distance of at least one imaging component of the medical imaging device, and
       image data of the imaged area; and
    the processing device is configured to determine the locational state based on the location information.

13. The medical imaging system of claim 1, wherein the processing device is configured to:
  receive information about the examination object, the information including information about at least one of a vessel structure of the examination object, a material property of the examination object or state information of the examination object; and
  determine the one or more control signals based on the information about the examination object.

14. The medical imaging system of claim 1, wherein
  the processing device is configured to repeatedly determine the one or more control signals based on at least another change in the imaged area or a change in the target position.

15. The medical imaging system of claim 1, wherein
  the medical imaging device is configured such that the location of the imaged area is settable by a user manually changing a position of the medical imaging device.

16. The medical imaging system of claim 1, wherein
  the medical imaging device includes a positioning device configured to robotically set the location of the imaged area.

17. The medical imaging system of claim 1, wherein
  the processing device is configured to control the medical imaging device based on movement information of the medical object.

18. The medical imaging system of claim 17, wherein the processing device is configured to control the medical imaging device based on movement information of the medical object including at least one of:
  performing an optimization of a mapping of the imaged area by adjusting one or more imaging parameters of the medical imaging device, the imaging parameter being among the one or more imaging parameters; or
  setting the location of the imaged area to include the medical object in the imaged area.

19. The medical imaging system of claim 1, wherein
  the medical imaging device includes an ultrasound imaging device with an ultrasonic device as an imaging component, the ultrasonic device being configured as an ultrasonic head for sonographic examination of the examination object.

20. The medical imaging system of claim 1, further comprising:
  a presentation device configured to display
    a first presentation of the imaged area, and
    a markings overlaid on the first presentation, the marking indicating the target position in the first presentation.

21. The m d imaging system of claim 1, wherein
  the processing device is configured to output a warning message to a user via a data interface of the processing device in response to an interruption to a data link, the data interface being a wireless data interface.

22. An intervention system for carrying out an interventional medical procedure, comprising:
  the medical imaging system of claim 1; and
  the movement device for robotic positioning of the medical object inside the examination object.

23. The intervention system of claim 22, wherein
  the movement device is configured to provide movement information relating to an instantaneous movement state of the medical object, the movement information including at least one of information relating to at least one of a speed, orientation, relative position or movement distance of the medical object; and
  the processing device is configured to determine the instantaneous position of the medical object based on the movement information.

24. The medical imaging system of claim 1, wherein the specification of the target position fixedly defines the target position relative to the image area, the specification of the target position causing the target position to change when the location of the imaged area changes.

25. The medical imaging system of claim 1, wherein the processing device is configured to change the location of the imaged area based on movement of the medical object.

26. The medical imaging system of claim 1, wherein the imaging parameter is a spatial radiation width, a propagation angle or a propagation direction.

27. A method for control of an imaging system, comprising:
  acquiring image data of an imaged area inside an examination object via an imaging device;
  determining an instantaneous position of a medical object;
  specifying a target position for the medical object, the target position being defined relative to the imaged area;
  determining one or more control signals for a movement device based on a change in a location of the imaged area, the one or more control signals being configured to cause a movement of the medical object from the instantaneous position to the target position via the movement device, and the change in the location of the imaged area including
    changing a position of the imaging device, or
    changing an imaging parameter of the imaging device; and
  providing the one or more control signals to the movement device.

28. A non-transitory computer program product, comprising:
  a program, directly loadable into a memory of a programmable arithmetic device of a processing device, the program including program segments that, when executed by the processing device, are configured to cause the processing device to;
  acquire image data of an imaged area inside an examination object via an imaging device,
  determine an instantaneous position of a medical object,
  specify a target position for the medical object, the target position being defined relative to the imaged area,
  determine one or more control signals for a movement device based on a change in a location of the imaged area, the one or more control signals being configured to cause a movement of the medical object from the instantaneous position to the target position via the movement device, and the change in the location of the imaged area including
    changing a positon of the imaging device, or
    changing an imaging parameter of the imaging device and
  provide the one or more control signals to the movement device.

* * * * *